(12) United States Patent
Muturi

(10) Patent No.: US 10,960,043 B1
(45) Date of Patent: Mar. 30, 2021

(54) NUTRITIOUS FRUIT JUICE SUPPLEMENT AND METHOD OF MAKING

(71) Applicant: John Muturi, The Woodlands, TX (US)

(72) Inventor: John Muturi, The Woodlands, TX (US)

(*) Notice: Subject to any disclaimer, the term of this patent is extended or adjusted under 35 U.S.C. 154(b) by 175 days.

(21) Appl. No.: 16/153,742

(22) Filed: Oct. 6, 2018

Related U.S. Application Data

(60) Provisional application No. 62/569,465, filed on Oct. 6, 2017.

(51) Int. Cl.
| | |
|---|---|
| A61K 36/00 | (2006.01) |
| A61K 36/74 | (2006.01) |
| A61K 9/48 | (2006.01) |
| A61K 9/19 | (2006.01) |
| A61K 36/185 | (2006.01) |
| A23L 2/02 | (2006.01) |
| A23L 33/105 | (2016.01) |
| A61K 9/00 | (2006.01) |

(52) U.S. Cl.
CPC .............. *A61K 36/74* (2013.01); *A23L 2/02* (2013.01); *A23L 33/105* (2016.08); *A61K 9/0056* (2013.01); *A61K 9/19* (2013.01); *A61K 9/48* (2013.01); *A61K 36/185* (2013.01); *A23V 2002/00* (2013.01)

(58) Field of Classification Search
None
See application file for complete search history.

*Primary Examiner* — Qiuwen Mi
(74) *Attorney, Agent, or Firm* — Serena Greene

(57) ABSTRACT

A nutritious fruit juice supplement with the major components coming from *Passiflora edulis* and *Galium aparine*, which contain several compounds including flavonoids, phenolic compounds, alkaloids, cyanogenic compounds, glycosides, vitamins A and C, riboflaurniacin, iron, magnesium, phosphorous, potassium, copper, terpenoid compounds, and protein. The innovating processing techniques increase the activity of antioxidant and anti-cancer properties already found in the fruit juice from *P. edulis* and *G. aparine* and create new compounds that should have additional antioxidant and anti-cancer properties.

1 Claim, 6 Drawing Sheets

|        | Fructose | Glucose | Sucrose |
|--------|----------|---------|---------|
| Purple | 33.5%    | 37.1%   | 29.4&   |
| Yellow | 29.4%    | 38.1%   | 32.4%   |

FIGURE 1

Sugar content of the different passion fruit cultivars

| Cultivar | Ripeness stage | Sugar content in juice of fruit (g kg⁻¹ fresh weight) | | | | |
|---|---|---|---|---|---|---|
| | | Non-reducing sugar | Reducing sugar | | | |
| | | Sucrose | Glucose | Fructose | G/F ratio | Total sugar (g kg⁻¹) |
| *Passiflora edulis* (Purple) | Vine-ripened | 13.11 ± 0.02d (10.74–15.39) | 66.33 ± 0.09a (64.52–67.35) | 64.65 ± 0.06a (63.75–65.38) | 1.03 | 142.85 ± 0.17a (138.33–144.86) |
| *Passiflora edulis* (Fredesich) | Vine-ripened | 10.22 ± 0.12f (9.67–10.41) | 33.73 ± 0.11c (32.26–35.84) | 33.72 ± 0.12c (32.11–36.04) | 1.00 | 77.73 ± 0.2c (74.67–82.19) |
| *Passiflora mollissima* | Vine-ripened | 17.08 ± 0.02c (16.71–18.43) | 23.42 ± 0.03e (22.76–23.92) | 22.14 ± 0.03d (21.51–22.54) | 1.06 | 62.63 ± 0.08d (60.97–63.84) |
| *Passiflora quadrangularis* | Vine-ripened | 28.19 ± 0.06b (27.41–29.45) | 43.73 ± 0.11b (42.26–45.85) | 39.07 ± 0.15b (36.67–41.78) | 1.12 | 111.05 ± 0.31b (106.27–116.86) |
| *Passiflora quadrangularis* ᵃ | Vine-ripened | 13.12 ± 0.02a (12.72–13.43) | 17.14 ± 0.03f (16.72–17.46) | 16.17 ± 0.02e (15.61–16.48) | 1.02 | 46.37 ± 0.07a (45.33–47.27) |
| *Passiflora edulis* (Yellow) | Vine-ripened | 15.39 ± 0.03a (14.75–15.77) | 65.68 ± 0.67a (64.63–66.49) | 58.61 ± 0.67a (57.46–59.49) | 1.12 | 139.69 ± 0.12a (137.75–141.98) |
| *Passiflora edulis* (Pink) | Non-vine-ripened | 45.51 ± 0.04a (44.73–46.06) | 30.17 ± 0.03d (29.54–30.55) | 31.13 ± 0.03c (30.75–31.82) | 0.96 | 106.91 ± 0.10b (103.94–108.33) |
| *Passiflora edulis* f. *flavicarpa* | Non-vine-ripened | 28.64 ± 0.01b (28.45–28.87) | 14.15 ± 0.01f (13.91–14.67) | 14.65 ± 0.01e (14.47–14.91) | 0.97 | 57.47 ± 0.03d (56.96–57.86) |

ᵃ Sugars from mesocarp.
Means in the same column with different letters (a–f) are statistically significant (Tukey's test, $P < 0.05$).

FIGURE 2

| Passion Fruit Nutrition Facts ||  |
|---|---|---|
| Principle | Nutrient Value | Percentage of RDA |
| Energy | 97 Kcal | 5% |
| Carbohydrates | 23.38g | 18% |
| Protein | 2.20g | 4% |
| Total Fat | 0.70g | 3% |
| Cholestorol | 0mg | 0% |
| Dietary Fiber | 10.40g | 27% |
| | | |
| Vitamins | | |
| Folates | 14mg | 3% |
| Niacin | 1.500mg | 9% |
| Pyridoxine | 0.100mg | 8% |
| Riboflavin | 0.130mg | 10% |
| Thiamin | 0.00mg | 0% |
| Vitamin A | 1274iu | 43% |
| Vitamin C | 30mg | 50% |
| Vitamin E | 0.02mg | <1% |
| Vitamin K | 0.7mg | 0.50% |
| | | |
| Electrolytes | | |
| Sodium | 0mg | 0% |
| Potassium | 348mg | 7% |
| | | |
| Minerals | | |
| Calcium | 12mg | 1.20% |
| Copper | 0.086mg | 9.50% |
| Iron | 1.60mg | 20% |
| Magnesium | 29mg | 7% |
| Phosphorous | 68mg | 10% |
| Selenium | 0.6mg | 1% |
| Zinc | 0.10mg | 1% |
| | | |
| Phyto-Nutrients | | |
| Carotene-beta | 743 micro g | |
| Crypto-xanthin-beta | 41 micro g | |
| Lycopene | 0 micro g | |

FIG. 3

| meq/100g | citric acid | malic acid | lactic acid | malonic acid | succinic acid | ascorbic acid |
|---|---|---|---|---|---|---|
| purple | 13.1 | 3.86 | 7.49 | 4.95 | 2.42 | 0.05 |
| yellow | 55 | 10.55 | 0.58 | 0.13 | trace | 0.06 |

FIGURE 4

| Sample Time | C. Received Lab | pH S.U. | Cu mg/kg dry wt | Pb mg/kg dry wt | Zn mg/kg dry wt | Al mg/kg dry wt | Ca mg/kg | Fe mg/kg dry wt | Mn mg/kg dry wt | Na mg/kg | pH S.U. |
|---|---|---|---|---|---|---|---|---|---|---|---|
| 08/28 10:30 | JM 09/04 12:21 | 5.37 | 5.5 | <1.0 | 27.0 | 222.9 | 12706.1 | 264.8 | 61.5 *1 | <400.0 | 6.64 |

Data Qualifiers: (1) J – estimated value, reported value associated QC were outside limits for accuracy and/or precision

FIGURE 5

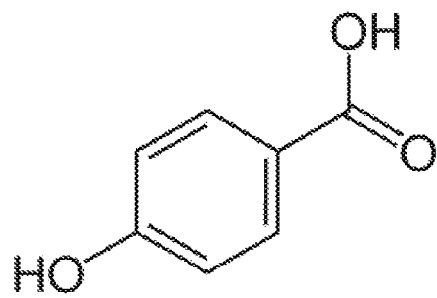

FIGURE 6

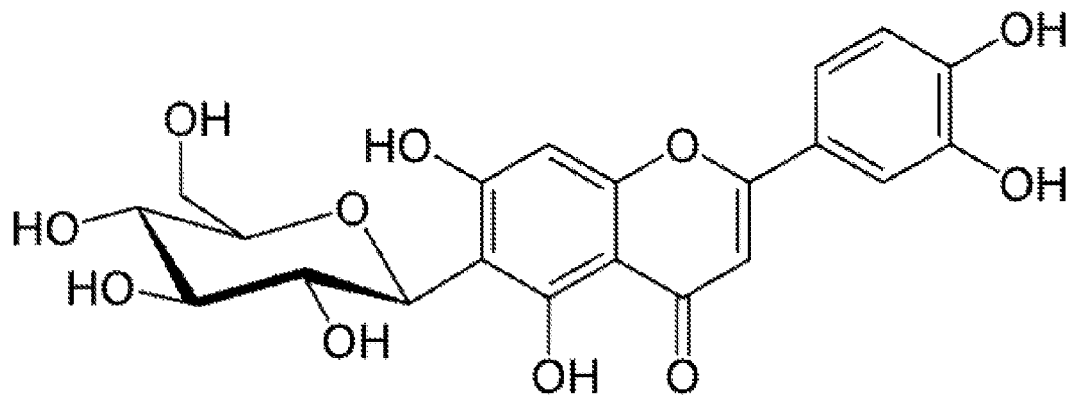

FIGURE 7

NUTRITIOUS FRUIT JUICE SUPPLEMENT AND METHOD OF MAKING

Priority is claimed from Provisional Application 62/569,465 files Oct. 6, 2017, which is hereby incorporated by reference.

BACKGROUND

The present application relates generally to a nutritious fruit juice supplement, and more specifically, to a nutritious fruit juice supplement which primary ingredients are passion fruit and an extract from *Galium aparine*.

Note that the points discussed below may reflect the hindsight gained from the disclosed inventions, and are not necessarily admitted to be prior art.

Passion fruit (*Passiflora edulis*) is an exotic climbing vine originating in South America. It is grown worldwide as an edible fruit for food industry. It has been used widely in folk medicine. The constituents of different extracts include flavonoids, alkaloids, cyanogenic compounds, glycosides, vitamins minerals and terpenoid compounds.

Passion fruit (*Passiflora edulis*) is an intriguing and mysterious fruit that has a surprising number of health and medicinal benefits for those who love the fruit. Some of these benefits include passion fruit ability to prevent cancerous growth among others such as boasting immune system, lowering blood pressure etc. Passion fruit also contains vitamins, A, C various flavonoids and phenolic compounds all of which have been linked to anti-cancer properties particularly in terms of oral and lung cancer.

The long list of benefits commonly attributed to passion fruit is due to the nutrient, mineral, and vitamin content of the fruit which include antioxidants, flavonoids, vitamins A and C, riboflaurniacin, iron, magnesium, phosphorous, potassium, copper, fiber and protein. The percentage of many of the vitamins and minerals are shockingly high.

*Passiflora edulis* is a vine species of passion flower is native to southern Brazil through Paraguay to Northern Argentina. It is cultivated commercially in tropical and subtropical areas for its sweet seedy fruit. The passion fruit is a type of berry, round to oval, either yellow or dark purple at maturity with a soft to firm juicy interior filled with numerous seeds. The fruit can be both eaten or juiced. Passion fruit powder can also be used to produce delectable smoothies and bubble tea drinks. It is often added to other fruit juices to enhance aroma.

The passion fruit is so called because it is one of the many species of passion flower, leading to the English translation of the latin genus name *Passiflora*. Around year 1700, the name was given by missionaries in Brazil as an educational aid while trying to convert the indigenous inhabitants to Christianity. Its name was flor das cinco Chagas or "flower of the five wounds". This was to illustrate the crucifixion of Jesus Christ, with other plant components also named after an emblem in the passion of Jesus Christ.

There are two varieties in the vine species of *Passiflora*. One is a shallow rooted woody perennial that possess many tendrils. The other variety is deeply rooted. The dark purple *edulis* variety is smaller than a lemon. It is less acidic than the yellow passion fruit and has a richer aroma and flavor.

SUMMARY

The present application discloses a nutritious fruit juice supplement (and related methods for making) with primary ingredients in the supplement being from dark purple *Passiflora edulis* and an extract from *Galium aparine*. Both ingredients have antioxidant and anti-cancer properties, in which the antioxidant and anti-cancer properties of the primary ingredients have been enhanced by changing the pH value and the interaction of the phenolic acid from the *Galium aparine* with the flavonoids from the fruit juice (*P. edulis* and other) along with the heavy metal enzyme-inhibitors from the *Galium asprine* extract which will form complexes with other compounds in the supplement which should have additional antioxidant and anti-cancer properties.

There are a number of innovative teachings disclosed in the present application. While these innovative teachings all combine synergistically, it should be noted that different innovations, and different subcombinations of these innovations, are all believed to be useful and nonobvious. No disclosed inventions, nor combinations thereof, are disclaimed nor relinquished in any way.

The present application teaches, among other innovations, a method for concentrating the nutritious fruit juice supplement without losing the antioxidant and anti-cancer properties of the primary ingredients.

In addition to the basic concepts listed above, many alternatives and modifications are also possible, by varying the amounts of secondary ingredients to make different flavors of the fruit juice supplement.

DESCRIPTION OF THE DRAWINGS

The novel features characteristic of the embodiments of the present application are set forth in the appended claims. However, the embodiments themselves, as well as a preferred mode of use and further objectives and advantages thereof, will best be understood by reference to the following detailed description when read in conjunction with the accompanying drawings, wherein:

FIG. 1 is a table showing the variation in sugar content between the two varieties of *Passiflora edulis;*

FIG. 2 is a table showing the variation in sugar content from vine-ripened and non-vine ripen juice between varieties of *Passiflora;*

FIG. 3 is a table showing Passion Fruit Nutritional Facts per 100 g;

FIG. 4 is a table showing the difference in acid content between the two varieties of *Passiflora edulis* displayed in milliequivalents per 100 g;

FIG. 5 is a metal analysis table for *Galium aparine;*

FIG. 6 is an example of the base structure of a phenolic acid;

FIG. 7 is the flavonoids is isoorientin;

DETAILED DESCRIPTION OF THE PREFERRED EMBODIMENT

Figure 8:
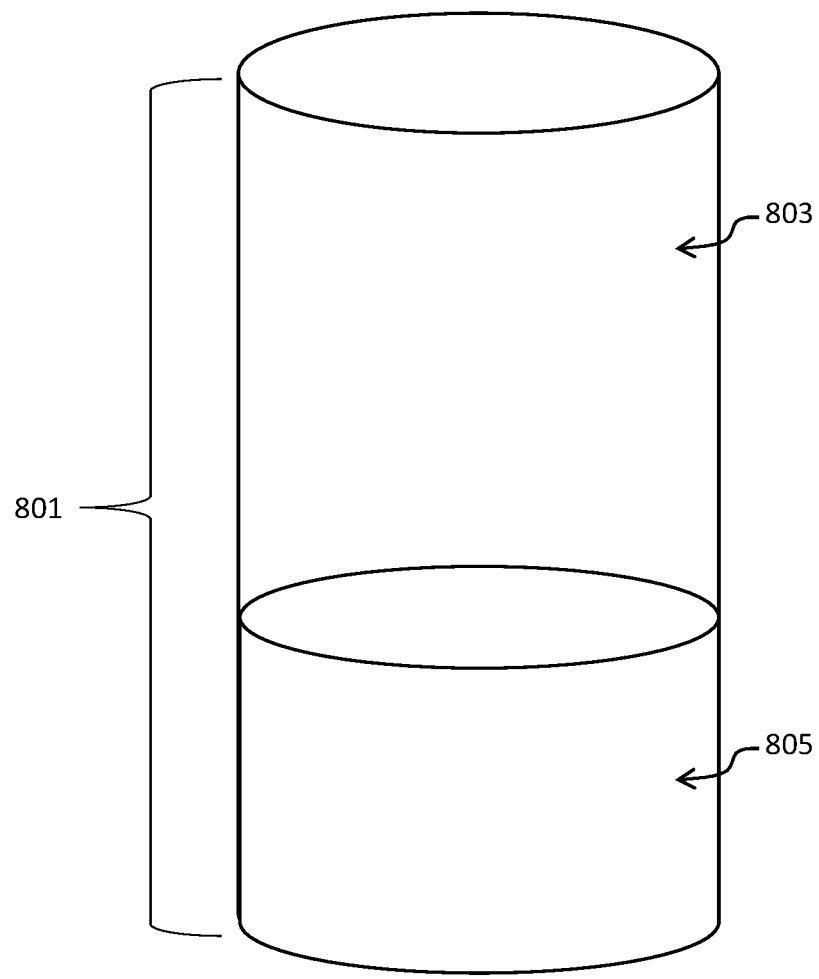
FIG. 8 is a depiction of a nutritious fruit juice supplement in accordance with a preferred embodiment of the present application.

Illustrative embodiments of a of the present application are provided below. It will of course be appreciated that in the development of any actual embodiment numerous implementation-specific decisions will be made to achieve the developer's specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The nutritious fruit juice supplement and method of making will be understood, both as to its components and procedures, from the accompanying drawings taken in conjunction with the accompanying description. Several embodiments of the nutritious fruit juice supplement and method of making are presented herein. It should be understood that various components, parts, and features of the various embodiments may be combined together and/or interchanged with one another; all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

The nutritious fruit juice supplement teaches of a supplement with main components of dark purple *Passiflora edulis* and an extract from *Galium aparine* having antioxidant and anti-cancer properties. The total carbohydrate content for *Passiflora edulis* is around 15-20% with slight variations between the purple and yellow varieties. The breakdown of the difference between the purple and yellow varieties of *Passiflora edulis* can be seen on FIG. 1. Because the purple variety of *Passiflora edulis* has slightly more fructose than sucrose, the juice from the purple variety has a lower impact on the production of insulin as fruit fructose is absorbed less rapidly because of the presence of fiber and other phytonutrients in the fruit. However, it should be noted that the sugar levels of the various types of sugars will vary depending on how ripe the fruit is and whether the fruit is ripened on the vine or off the vine. Vine ripened fruit will have a lower sucrose level compared to non-vine ripened fruit FIG. 2.

FIG. 3 is a chart of the nutritional analysis of the *Passiflora edulis*. *Passiflora edulis* is rich in vitamin C, vitamin A, Iron, phosphorus, riboflavin, copper, niacin, pyridoxine, magnesium and potassium FIG. 3. Many of the compounds found in *Passiflora edulis* are useful for enzymatic processes.

*P. edulis* has a high acid content. The breakdown of the acid content is shown in the table of FIG. 4. The high acid content gives the juice a pH value around 3. During the processing of the supplement the pH will speed up the antioxidant and anti-cancer properties found in the supplement.

The phenolic acid from *G. aparine* will interact with the flavonoids in *P. edulis* to further increase the potency of the supplement and provide more antioxidant agents to enhance the antioxidant/anti-cancer activity. *G. aparine* has several types of phenolic acid, but the basic structure of a phenolic acid comprises of a phenolic ring and an organic carboxylic acid function. FIG. 5 is a metal analysis table for *G. aparine*, which shows the metal content of several key minerals that have biological functions. FIG. 6 shows a simple phenolic acid, p-hydroxybenzoic acid. *P. edulis* has many flavonoids, one of the primary flavonoids is isoorientin FIG. 7. Under the proper conditions the carboxylic acid of the phenolic acid bond with an OH group on the isoorientin.

FIG. 8 depicts a nutritious fruit juice supplement 801 in in accordance with a preferred embodiment. The nutritious fruit juice supplement 801 is comprised of a *Galium aparine* extract 803 and a *Passiflora edulis* extract 805. In the preferred embodiment the ratio between the *Galium aparine* extract 803 and a *Passiflora edulis* extract 805 is 3:2. It should be appreciated that different ratios may be considered for other embodiments and taste reasons. In the preferred embodiment extracts 803 and 805 are mixed together and refrigerated between 35° F. and 40° F. until consumption. Recommended consumption is twice a day, 10 ounces or the equivalent of 10 ounce of the nutritional fruit supplement 701.

The *Galium aparine* extract 803 is the result of a 1 to 45 ratio of dried *Galium aparine* plant to purified water. The plant and water combination are then boiled at an average temperature of 95° C. for 30 to 45 minutes until a clear dark solution is obtained, when the solid plant matter is removed from the *Galium aparine* extract. The pH of the extract is 5.59±0.05. The *Galium aparine* extract 803 is then stored between 1.6° C. and 4.4° C. until use or further processing.

The *Passiflora edulis* extract 805 is the result of taking very ripe purple kind of *Passiflora edulis*. Ripe *Passiflora edulis* will be crinkly and slightly soft. The fruit must be thoroughly clean with fresh water to remove any contamination on the skin and inspected to ensure that there is no moldy fruit or otherwise undesirable fruit used in making the *Passiflora edulis* extract 805. The flesh jelly of each fruit is removed along with the seeds and place in a blender with purified water approximately 3 times the amount of the flesh and seeds and blended at a low speed for a minute or so until the seeds separate from the jelly and settle to the bottom of the mixture. Special care must be taken not to over blend, which can cause the breaking of the seeds. After separation of the seeds from the jelly the *Passiflora edulis* extract 805 is separated from the seeds by pouring the mixture through a sieve and pressing out all the liquid. The *Passiflora edulis* extract 705 is then stored between 1.6° C. and 4.4° C. until use or further processing.

Figure 9:
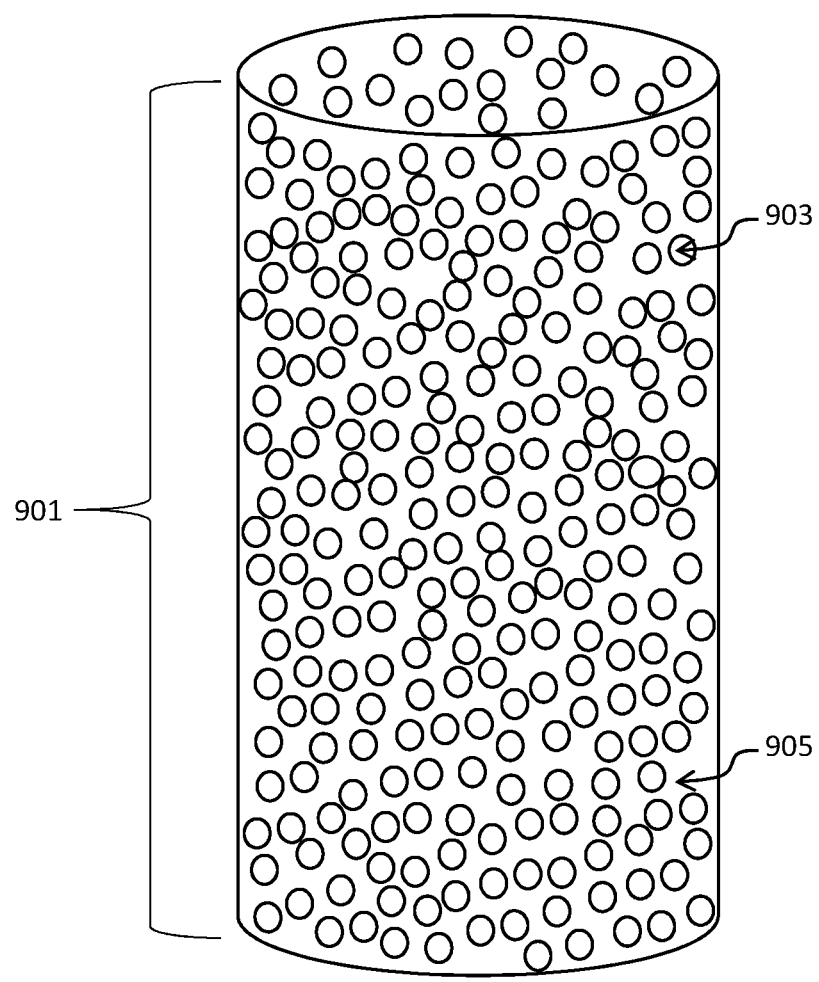
FIG. 9 is a depiction of the nutritional supplement in accordance with an alternative embodiment of the present application While the nutritious fruit juice supplement and method of making in the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives

FIG. 9 depicts an alternative embodiment of the nutritional fruit juice supplement 901. The nutritional fruit juice supplement 901 is comprised of a *Galium aparine* extract spheres 903 in a *Passiflora edulis* extract 905. The ratio between *Galium aparine* extract sphere 903 in a *Passiflora edulis* extract 905 is 1:1. It should be appreciated that different ratios may be considered for other embodiments and taste reasons and that the dilution of the nutritional fruit juice supplement 901 may be required by some users. Recommended consumption is twice a day, 10 ounces or the equivalent of 10 ounce of the nutritional fruit supplement 801.

The method for preparing the *Galium aparine* extract spheres 903 begins by starting with the *Galium aparine* extract 803. The *Galium aparine* extract 803 is further concentrated through reflux. For example, start with 10 grams of dried *Galium aparine* plant matter, add 450 milliliters of purified water and boil the mixture at an average temperature of 95° C. for ~40 minutes until a clear dark solution is obtained. After the solid plant mater is removed, the amount of *Galium aparine* extract 803 is approximately 190 milliliters. It should be appreciated that the collected amount at the initial extraction stage can vary depending on overall conditions. After further concentration using reflux for ~20 minutes the resulting *Galium aparine* extract is now concentrated to 100 milliliters.

The *Galium aparine* extract spheres 903 are created using edible polysaccharides as a scaffold to contain the concentrated *Galium aparine* extract, while using the water in the concentrated *Galium aparine* extract to hydrate the polysaccharides. It should be appreciated that in other embodiments the unconcentrated form of the *Galium aparine* extract may be used and other liquid may also be added for flavor or nutrition including the *Passiflora edulis* extract 905.

One method of creating the *Galium aparine* extract spheres 903 is by emulsifying 0.5% w/v of sodium alginate into the concentrated *Galium aparine* extract. After the air bubbles are removed the mixture is dropped into a 1% solution of calcium chloride (or calcium lactate, calcium salt, etc.) that was prepared with distilled water. The drops should form spheres with a diameter less than 8 mm and a diameter less than 4 mm is preferred. The spheres are bathed in the calcium chloride solution for 1 to 2 minutes before being removed and rinsed twice in clean distilled water.

Another method of creating the *Galium aparine* extract spheres 903 is to heat the concentrated *Galium aparine* extract to ~90° C. and add 1.5% to 2.5% w/w agar and stir until complete dissolve. Then the resulting mixture is slightly cooled. After the mixture is cooled, the mixture is dropped into a chilled oil bath (edible/non-toxic oil at ~20-25° C.). The drops should form spheres with a diameter less than 8 mm and a diameter less than 4 mm is preferred. The spheres are bathed in the oil bath for 2 to 4 minutes before being removed and rinsed twice in clean distilled water.

After processing the *Galium aparine* extract spheres 903 are stored moist between 1.6° C. and 4.4° C. in an air tight container until ready to use.

Other embodiments of the nutritious fruit juice supplement may have the *Galium aparine* extract 803 and/or the *Passiflora edulis* extract 805 in a dried form. The dried form of the extracts 803, 805 may be achieved by freeze, spray or another method of drying liquids. The extracts 803, 805, and spheres 903 may be packaged separately or together in the dry form for addition into edible liquid or for further processing. The further processing may include encapsulation of the dry extracts. Other processing of the nutritious fruit juice supplement 801 and/or the extracts 803, 805, and the spheres 903 which may or may not be in a dry form may include being made into a solid edible piece.

In addition, it should be appreciated that another unique feature is the variety of ways which the supplement can be processed for use to reach the end consumer.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An encapsulated nutritious fruit juice supplement comprising:
    three parts concentrated *Galium aparine* extract; and
    two parts *Passiflora edulis* extract.

* * * * *